__US005087630A__

United States Patent [19]

Colle et al.

[11] Patent Number: 5,087,630
[45] Date of Patent: Feb. 11, 1992

[54] METHOD FOR THE TREATMENT OF A HYPONATRAEMIC DISEASE

[75] Inventors: Roberto Colle; Antonio Pizzi; Geoffrey D. Clarke, all of Milan, Italy

[73] Assignee: Dr. Lo. Zambeletti SpA, Italy

[21] Appl. No.: 422,122

[22] Filed: Oct. 16, 1989

[30] Foreign Application Priority Data

Oct. 17, 1988 [GB] United Kingdom ............... 8824291

[51] Int. Cl.$^5$ .................. A61K 31/47; A61K 31/445; A61K 31/44
[52] U.S. Cl. ................................ 514/307; 514/315; 514/316; 514/869; 514/326; 514/343
[58] Field of Search ............... 514/186, 187, 307, 315, 514/316, 869; 546/146

[56] References Cited

FOREIGN PATENT DOCUMENTS 0228246 7/1987 European Pat. Off. .
0232989 8/1987 European Pat. Off. .

OTHER PUBLICATIONS

Chemical Abstracts (vol. 107:236532d) 1987.
Chemical Abstracts (vol. 108:37666w) 1988.

Primary Examiner—Frederick E. Waddell
Assistant Examiner—Kevin Weddington
Attorney, Agent, or Firm—Rosenman & Colin

[57] ABSTRACT

Compounds of formula (Ia), or pharmaceutically acceptable salts or solvates thereof,

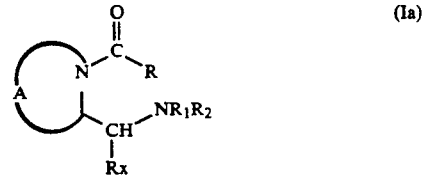

in which
A, together with the nitrogen atom, represents —(CH$_2$)$_p$—, where p is an integer from 3 to 6, or an optionally substituted tetrahydroisoquinoline ring system;
each of R$_1$ and R$_2$ are independently hydrogen, C$_{1-6}$ alkyl, C$_{2-6}$ alkenyl C$_{3-6}$ cycloalkyl or C$_{4-12}$ cycloalkylalkyl, or together form a C$_{2-6}$ polymethylene or C$_{2-6}$ alkenylene group, optionally substituted with a hetero-atom,
R$_x$ is hydrogen, C$_{1-6}$ alkyl or phenyl, or together with R$_1$ forms a —(CH$_2$)$_3$— or —(CH$_2$)$_4$— group; and R comprises a substituted or unsubstituted carbocyclic or heterocyclic aromatic group;
and compounds of formula (Ib)

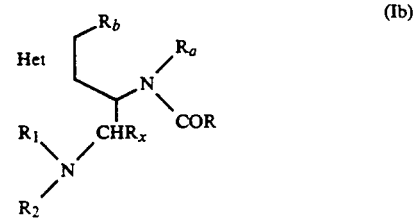

in which:
R, R$_1$, R$_2$ and X are as defined in formula (Ia)
R$_a$ is C$_{1-6}$ alkyl or phenyl;
R$_b$ is hydrogen or together with R$_a$ forms a —(CH$_2$)$_n$— group in which n=1, 2 or 3; and
'Het' is an optionally substituted single or fused ring heterocyclic group containing from 5 to 12 ring atoms and comprising up to four hetero-atoms in the or each ring, selected from oxygen, nitrogen and sulphur,
are useful as diuretic agents.

8 Claims, No Drawings

METHOD FOR THE TREATMENT OF A HYPONATRAEMIC DISEASE

The present invention relates to the use of certain compounds for the manufacture of medicaments for the treatment of hyponatraemic disease states; to a method of treatment of hyponatraemic disease states; and to pharmaceutical compositions for the treatment of such disease states.

EP-A-0228246, 0232612, 0232989, 0260041, 0275696, 0330360, 0333315 and 0333427 (all Dr. Lo. Zambeletti S.p.a.) describe classes of azacyclic and isoquinoline derivatives which exhibit kappa receptor agonism and are of potential therapeutic utility as analgesics.

It has now been found that compounds of these classes have diuretic activity which indicates that they are of potential use in the treatment of hyponatraemic disease states in mammals.

According to the present invention there is provided the use of a compound of formula (Ia) or (Ib), or a pharmaceutically acceptable salt or solvate thereof, for the manufacture of a medicament for the treatment of hyponatraemic disease states, formula (Ia) being:

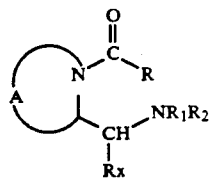

in which

A, together with the nitrogen atom, represents $-(CH_2)_p-$, where p is an integer from 3 to 6, or an optionally substituted tetrahydroisoquinoline ring system;

each of $R_1$ and $R_2$ are independently hydrogen, $C_{1-6}$ alkyl, $C_{2-6}$ alkenyl $C_{3-6}$ cycloalkyl or $C_{4-12}$ cycloalkylalkyl, or together form a $C_{2-6}$ polymethylene or $C_{2-6}$ alkenylene group, optionally substituted with a heteroatom, $R_x$ is hydrogen, $C_{1-6}$ alkyl or phenyl, or together with $R_1$ forms a $-(CH_2)_3-$ or $-(CH_2)_4-$ group; and R comprises a substituted or unsubstituted carbocyclic or heterocyclic aromatic group; and formula (Ib) being:

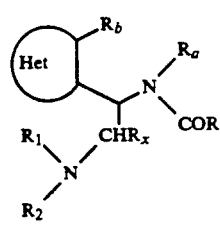

in which:

R, $R_1$, $R_2$ and X are as defined in formula (Ia)

$R_a$ is $C_{1-6}$ alkyl, preferably methyl or ethyl, or phenyl;

$R_b$ is hydrogen or together with $R_a$ forms a $-(CH_2)_n-$ group in which n=1, 2 or 3; and 'Het' is an optionally substituted single or fused ring heterocyclic group, preferably having aromatic character, containing from 5 to 12 ring atoms and comprising up to four hetero-atoms in the or each ring, selected from oxygen, nitrogen and sulphur.

When used herein, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

Preferably, 'Het' in formula (Ib) is a single ring containing one or two sulphur or nitrogen atoms.

When $R_1$ and $R_2$ are $C_{1-6}$ alkyl groups, examples are methyl, ethyl, propyl, butyl, pentyl or hexyl groups, preferably methyl.

Examples of $C_{2-6}$ alkenyl groups are 1- and 2- propenyl; an example of a $C_{3-6}$ cycloalkyl group is cyclopropyl, and an example of a $C_{4-12}$ cycloalkylalkyl group is cyclopropylmethyl. When $R_1$ and $R_2$ together form a polymethylene group, examples are propylene, butylene, pentylene or hexylene, preferably butylene. As an alkenylene group, $R_1$-$R_2$ may be typically $-CH_2-CH=CH-CH_2-$. Examples of hetero-atoms are oxygen and sulphur, particularly oxygen, and suitable hetero-atom substituted polymethylene group is $-CH_2CH_2OCH_2CH_2-$.

When A in formula (Ia) forms an optionally substituted tetrahydroisoquinoline ring system with the nitrogen atom, the system preferably has the formula (IIa)

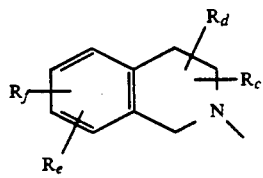

in which:

$R_c$ and $R_d$, which may be the same or different and may be attached to the same or different carbon atoms of the isoquinoline nucleus, are each hydrogen, halogen, preferably fluorine, hydroxy, $C_{1-6}$ alkyl, preferably methyl or ethyl, aryl, preferably optionally substituted phenyl, or $R_c$ together with $R_d$ form a $-(CH_2)_q-$ group, where q is an integer of from 1 to 5 and one or more of the $-(CH_2)-$moieties is optionally substituted by a $C_{1-6}$ alkyl group, $R_e$ and $R_f$, which may be the same or different, are each hydrogen, $C_{1-6}$ alkyl, $-CH_2OR_{6m}$, halogen, hydroxy, $C_{1-6}$ alkoxy, $C_{1-6}$ alkoxycarbonyl, thiol, $C_{1-6}$ alkylthio

$-NHCOR_{6p}$, $-NHSO_2R_{6q}$, $-CH_2SO_2NR_{6r}R_{6s}$, in which each of $R_{6m}$ to $R_{6s}$ is independently hydrogen, $C_{1-6}$ alkyl, aryl (preferably phenyl) or aralkyl (preferably phenyl $C_{1-6}$ alkyl).

The group R in formulae I(a) and I(b) preferably has the formula (IIb)

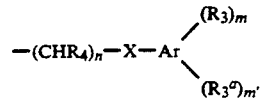

in which n is 0, 1 or 2, m is 0, 1 or 2, m' is 0, 1 or 2, provided m+m'<2;

X is a direct bond, or O, S or $NR_5$ in which $R_5$ is hydrogen or $C_{1-6}$ alkyl;

Ar is a substituted or unsubstituted carbocyclic aromatic or heterocyclic aromatic group, each of $R_3$ and $R_3{}^a$ is an electron withdrawing substituent, $C_{1-6}$ alkoxy, $C_{1-6}$ haloalkoxy, $C_{1-6}$ alkyl, $C_{1-6}$ haloalkyl, $C_{1-6}$ haloalkenyl, $C_{1-6}$ haloalkynyl, aryl (preferably phenyl) or halogen or, when m is 2, two $R_3$'s form a $C_{3-6}$ polymethylene group;

and $R_4$ is hydrogen or $C_{1-6}$ alkyl.

Examples of $R_3$ or $R_3{}^a$ are $-NO_2$, $-CN$, $-CF_3$, $-Cl$, $Br$, $-OCF_3$, $-OCHF_2$, $-OCF_2CF_2H$, $-OCCl_2CF_3$, $-COOR_6$, $-CONR_7R_8$, $-SO_3R_9$, $-SO_2NR_{10}R_{11}$ and $-COR_{12}$ in which each of $R_6$ to $R_{12}$ is independently hydrogen, $C_{1-6}$ alkyl, aryl or aralkyl. When two $R_3$'s are linked they may form a fused cyclopentyl or cyclohexyl ring.

Examples of $R_4$ are methyl and ethyl, and preferably $R_4$ is hydrogen.

Preferably Ar is phenyl and $R_3$ or $R_3{}^a$ is preferably in the meta- and/or para- position.

Preferably, $R_3$ or $R_3{}^a$ is bromine, chlorine, $-NO_2$ or $-CF_3$, particularly in the meta- or para-position.

X is typically oxygen or a direct bond, and n is typically 0 or 1.

In the compounds of formula (Ia), R may also have the formula (IIc)

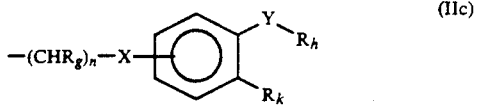

(IIc)

in which the group $-(CHR_g)_n-X-$ is in the meta- or paraposition with respect to $YR_h$ or $R_k$; $R_g$ is hydrogen or $C_{1-6}$ alkyl, preferably hydrogen; n and X are as defined in formula (IIb), Y is >C=O, >CHOH, $-S=O$ or $SO_2$;

each of $R_h$ and $R_k$ is $C_{1-6}$ alkyl, or $R_h$ and $R_k$ are linked together and $R_h$ represents $-(Z)m$-where m is 0 or 1 and Z is O, S or $NR_s$ where $R_s$ is hydrogen or $C_{1-6}$ alkyl, and $R_k$ represents $-(CH_2)_r-$ where r is an integer of from 1 to 4, preferably 2 or 3, and in which one or more of the $-(CH_2)-$ groups is optionally substituted by a $C_{1-6}$ alkyl group.

Examples of R are:

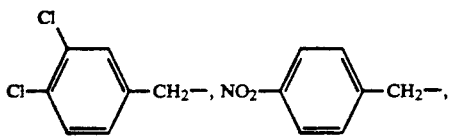

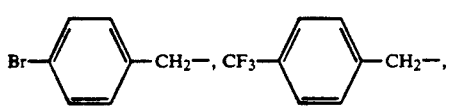

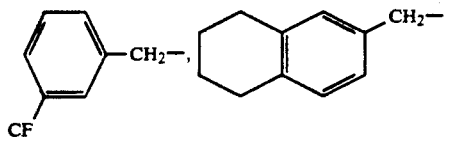

Examples of sub-groups of compounds within formula (Ia) are compounds of formulae (Ic) and (Id):

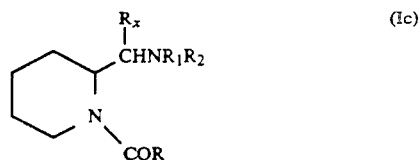

(Ic)

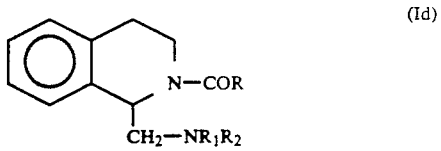

(Id)

in which R, $R_1$, $R_2$ and $R_x$ are as defined with reference to formula (Ia).

In a further aspect of the invention there is provided a pharmaceutical composition for use in the treatment of hyponatraemic disease states in mammals which comprises a compound of formula (Ia) or (Ib) (as hereinbefore defined) or a pharmaceutically acceptable salt or solvate thereof, (hereinafter referred to as the Compound) and a pharmaceutically acceptable carrier.

The invention further provides a method for the treatment and/or prophylaxis of hyponatraemic disease states in mammals, particularly humans, which comprises administering to the mammal in need of such treatment and/or prophylaxis an effective amount of the Compound.

The Compound is in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the Compound.

One preferred pharmaceutically acceptable form is the crystalline form, including such form in a pharmaceutical composition. In the case of salts and solvates the additional ionic and solvent moieties must also be non-toxic.

Examples of the Compound in the form of a pharmaceutically acceptable salt include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

An example of the Compound in the form of a pharmaceutically acceptable solvate includes the hydrate.

The Compounds have at least two asymmetric centres and therefore exist in more than one stereoisomeric form. The invention extends to the use of all such forms and to mixtures thereof, including racemates.

The Compounds may be prepared as described in the aforementioned documents, EP-A-0228246, 0232612, 0232989, 0260041, 0275696, 0330360, 0333315 and 0333427 (the subject matter of which are incorporated herein by reference) or by analogous methods thereto.

Medicaments and compositions containing the Compounds may be prepared by admixture of a Compound with an appropriate carrier, which may contain a diluent, binder, filler, disintegrant, flavouring agent, colouring agent, lubricant or preservative in conventional manner.

These conventional excipients may be employed for example as in the preparation of compositions of known diuretic agents.

Preferably, a medicament or pharmaceutical composition of the invention is in unit dosage form and in a form adapted for use in the medical or veterinarial fields. For example, such preparations may be in a pack form accompanied by written or printed instructions for use as a diuretic agent.

The suitable dosage range for a Compound depends on the Compound to be employed and on the condition of the patient. It will also depend, inter alia, upon the relation of potency to absorbability and the frequency and route of administration.

The Compound may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The Compounds may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

The effective dose of Compound depends on the particular Compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20mg of active ingredient and be administered in multiples, if desired, to give the preceding daily dose.

Within the above indicated dosage range, no adverse toxicological effect have been observed with the Compounds in tests which are indicative of compounds of potential use as diuretic agents.

The following pharmacological data illustrate the activity of Compounds in tests which are indicative of Compounds of potential use as diuretic agents.

Compound 1 is -(2S)-1-(3,4,-dichlorophenylacetyl)-2-(1-pyrrolidinylmethyl)piperidine hydrochloride hydrate (the compound of Example 4 of EP-A-0232612)

Compound 2 is (2R,S)-1-(4-nitrophenylacetyl)-2-(1pyrrolidinylmethyl)piperidine hydrochloride (the compound of Example 4 of EP-A-0260041)

Compound 3 is (2S)-1-(4-trifluoromethylphenylacetyl)-2-(1-pyrrolidinylmethyl)piperidine hydrochloride sesquihydrate (the compound of Example 3 of EP-A-0260041)

Compound 4 is 1-(1-pyrrolidinylmethyl)-2-(3,4-dichlorophenylacetyl)-1,2,3,4-tetrahydroisoquinoline hydrochloride (the compound of Example 7(d) of EP-A-0232989)

Compound 5 is (−)-1-(1-pyrrolidinylmethyl)-2-(3,4-dichlorophenylacetyl)-1,2,3,4-tetrahydroisoquinoline (−)-tartrate (the compound of Example 9 of EP-A-0232989)

Compound 6 is (−)-1-(1-pyrrolidinylmethyl)-2-(4-trifluoromethylacetyl)-1,2,3,4-tetrahydroisoquinoline (the (−) enantiomer of the compound of Example 14 of EP-A-0232989)

Compound 7 is 1-[1-oxo-3,4,-dihydro-(2H)-naphth-6-yl]-acetyl-2(pyrrolidin-1-yl) methyl-piperidine hydrochloride (the compound of Example 1 of EP-A-0333315)

Compound 8 is 1(pyrrolidin-1-yl)methyl-2-(3,4-dichlorophenyl)acetyl-5-hydroxy-1,2,3,4-tetrahydroisoquinoline (the compound of Example 5 of EP-A-0330360)

Compound 9 is 4-(pyrrolidin-1-yl)methyl-5-(3,4-dichlorophenyl)acetyl-4,5,6,7-tetrahydrothieno[3,2-c]-pyridine hydrochloride monohydrate (the compound of Example 3 of EP-A-0333427)

Compound 10 is 4-(piperidin-1-yl)methyl-5-(3,4-dichlorophenyl)acetyl-4,5,6,7-tetrahydrothieno[3,2-c]-pyridine hydrochloride (the compound of Example 5 of EP-A-0333427)

Pharmacological Data

Introduction

The diuretic activity of each of the Compounds 1 to 10 was assessed by measuring the urine output in normally-hydrated and water-loaded rats according to the methods of Leander J. D. (1) and of Hayes A. G. (2) respectively.

Methods

Male Sprague-Dawley rats (250–400 g) were used, after at least one week of acclimatization, and were starved overnight on the eve of the experiment.

In the normally-hydrated paradigm, the animals, 3-4-5 per group, were randomly injected subcutaneously with the test Compound or solvent, and then put in individual glass diuresis cages and the urine collected hourly for 5-6-7 hours.

In the water-loaded paradigm, the animals were loaded orally with 25 ml/kg of tap water 10 minutes before treatment with the test Compound.

During the test period neither food nor water were allowed. Data were expressed in terms of ml of urine output and significance calculated using the Student "t" test.

References

1) LEANDER J. D.-J. Pharmacol. Exp. Ther. 224, 89, 1983
2) HAYES A. G. - J Pharmacol. Exp. Ther. 240, 984, 1987

| Compound No. | No. of Animals | Dose mg/Kg s·c | Duration hours | Results Normally hydrated | Water loaded |
|---|---|---|---|---|---|
| 1 | (3) | — | 5 | | 8.3 ± 0.63 |
| | 3 | 0.012 | 5 | | 12.4 ± 1.31* |
| | 3 | 0.060 | 5 | | 21.8 ± 0.85*** |
| | 3 | 0.300 | 5 | | 22.1 ± 4.04* |
| | 3 | 1.5 | 5 | | 26.0 ± 1.22*** |
| 2 | (2) | — | 5 | | 7.7 |
| | 3 | 0.011 | 5 | | 9.3 ± 0.94 |
| | 3 | 0.054 | 5 | | 10.4 ± 0.45 |
| | 3 | 0.270 | 5 | | 14.8 ± 1.26 |
| | 3 | 0.899 | 5 | | 22.4 ± 1.32 |
| 3 | (4) | — | 5 | 1.8 ± 0.50 | 10.2 ± 0.69 |
| | 4 | 0.0022 | 5 | 2.1 ± 0.33 | 10.7 ± 0.98 |
| | 4 | 0.011 | 5 | 4.3 ± 1.55* | 13.5 ± 1.11* |
| | 4 | 0.054 | 5 | 7.1 ± 0.84** | 15.9 ± 0.63*** |
| | 4 | 0.272 | 5 | 14.2 ± 2.06** | 22.8 ± 1.52*** |
| | 4 | 0.905 | 5 | — | 22.9 ± 2.13** |
| 4 | (2) | — | 5 | | 9.4 |
| | 3 | 0.011 | 5 | | 16.7 ± 1.87 |
| | 3 | 0.055 | 5 | | 26.1 ± 1.50 |
| | 3 | 0.275 | 5 | | 25.5 ± 1.25 |
| | 2 | 0.916 | 5 | | 24.9 |
| 5 | (3) | — | 5 | | 8.1 ± 1.81 |
| | 3 | 0.009 | 5 | | 23.2 ± 2.19** |
| | 3 | 0.044 | 5 | | 23.1 ± 1.67** |
| | 3 | 0.219 | 5 | | 23.9 ± 3.12* |
| | 3 | 0.729 | 5 | | 27.0 ± 3.06** |
| 6 | (3) | — | 5 | | 7.9 ± 0.13 |
| | 3 | 0.012 | 5 | | 15.5 ± 1.96** |
| | 3 | 0.060 | 5 | | 22.2 ± 1.70** |
| | 3 | 0.300 | 5 | | 23.1 ± 5.75 |
| | 2 | 1.000 | 5 | | 23.2 |
| 7 | 3 | — | 5 | | 8.3 ± 0.33 |
| | 3 | 0.011 | 5 | | 10.6 ± 1.72 |
| | 3 | 0.055 | 5 | | 11.0 ± 2.63 |
| | 3 | 0.275 | 5 | | 9.7 ± 0.85 |
| | 3 | 0.938 | 5 | | 18.7 ± 1.74***° |
| | 3 | 9.380 | 5 | | 15.8 ± 2.70° |
| 8 | 5 | — | 7 | 1.9 ± 0.35 | 9.9 ± 0.47 |
| | 5 | 0.0005 | 7 | 3.8 ± 0.81 | 12.6 ± 0.89* |
| | 5 | 0.0024 | 7 | 11.3 ± 0.71*** | 18.5 ± 0.16***° |
| | 5 | 0.012 | 7 | 14.7 ± 1.22*** | 21.5 ± 1.35*** |
| | 5 | 0.06 | 7 | 17.6 ± 0.85*** | 25.7 ± 2.8*** |
| 9 | 4 | — | 5 | | 10.1 ± 1.80 |
| | 4 | 0.0021 | 5 | | 17.4 ± 0.55** |
| | 4 | 0.011 | 5 | | 21.5 ± 1.42** |
| | 3 | 0.053 | 5 | | 21.4 ± 4.07 |
| | 4 | 0.264 | 5 | | 25.9 ± 2.50** |
| | 4 | 0.881 | 5 | | 15.7 ± 2.33° |
| 10 | 4 | — | 6 | 2.6 ± 0.35 | 9.9 ± 1.68 |
| | 4 | 0.013 | 6 | 4.6 ± 0.63* | 13.7 ± 0.29** |
| | 4 | 0.066 | 6 | 9.9 ± 1.49** | 16.5 ± 1.41** |
| | 4 | 0.330 | 6 | 15.4 ± 0.92*** | 21.3 ± 0.69***° |
| | 4 | 1.7 | 6 | 16.7 ± 1.59*** | 20.8 ± 0.67***° |

*p < 0.05;
**p < 0.01;
***p < 0.001
°Separate experiment
No. of animals in brackets refer to control animals

We claim:

1. A method for the treatment of hyponatraemic disease states in mammals, which comprises administering to the mammal in need of such treatment an effective amount of a compound of formula (Ia), or a pharmaceutically acceptable salt or solvate thereof, formula (Ia) being:

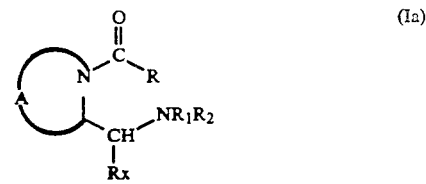

in which

A, together with the nitrogen atom, represents —$(CH_2)p$—, where p is an integer from 3 to 6, or an optionally substituted tetrahydroisoquinoline ring system;

each of $R_1$ and $R_2$ are independently hydrogen, $C_{1-6}$ alkyl, $C_{2-6}$ alkenyl $C_{3-6}$ cycloalkyl or $C_{4-12}$ cycloalkylalkyl, or together form a $C_{2-6}$ polymethylene or $C_{2-6}$ alkenylene group, optionally substituted with a hetero-atom, $R_x$ is hydrogen, $C_{1-6}$ alkyl or phenyl, or together with $R_1$ forms a —$(CH_2)_3$— or —$(CH_2)_4$— group; and R comprises a substituted or unsubstituted carbocyclic or heterocyclic aromatic group.

2. A method according to claim 1 in which each of $R_1$ and $R_2$ is methyl, ethyl, propyl, butyl, pentyl, hexyl, 1- or 2- propenyl, cyclopropyl, cyclopropylmethyl, or $R_1$ and $R_2$ together form a propylene, butylene, pentylene or hexylene group.

3. A method according to claim 1 in which

in formula (Ia) has the formula

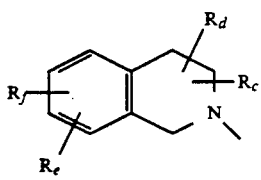

(IIa)

in which:

$R_c$ and $R_d$, which may be the same or different and may be attached to the same or different carbon atoms of the isoquinoline nucleus, are each hydrogen, halogen, hydroxy, $C_{1-6}$ alkyl or aryl, or $R_c$ together with $R_d$ form a $-(CH_2)_q-$ group, where $q$ is an integer of from 1 to 5 and one or more of the $-(CH_2)-$ moieties is optionally substituted by a $C_{1-6}$ alkyl group, $R_e$ and $R_f$, which may be the same or different, are each hydrogen, $C_{1-6}$ alkyl, $-CH_2OR_{6m}$, halogen, hydroxy, $C_{1-6}$ alkoxy, $C_{1-6}$ alkoxycarbonyl, thiol, $C_{1-6}$ alkylthio,

$-NHCOR_{6p}$, $-NHSO_2R_{6q}$, $-CH_2SO_2-SO_2NR_{6r}R_{6s}$, in which each of $R_{6m}$ to $R_{6s}$ is independently hydrogen, $C_{1-6}$ alkyl, aryl or aralkyl.

4. A method according to claim 1 in which R in formulae I(a) has the formula (IIb)

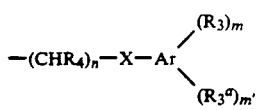

(IIb)

in which
n is 0, 1 or 2,
m is 0, 1 or 2,
m' is 0, 1 or 2, provided m+m'<2;
X is a direct bond, or O, S or $NR_5$ in which $R_5$ is hydrogen or $C_{1-6}$ alkyl;
Ar is a substituted or unsubstituted carbocyclic aromatic or heterocyclic aromatic group,
each of $R_3$ and $R_3{}^a$ is an electron withdrawing substituent, $C_{1-6}$ alkoxy, $C_{1-6}$ haloalkoxy, $C_{1-6}$ alkyl, $C_{1-6}$ haloalkyl, $C_{1-6}$ haloalkenyl, $C_{1-6}$ haloalkynyl, aryl or halogen or, when m is 2, two $R_3$'s form a $C_{3-6}$ polymethylene group;

and $R_4$ is hydrogen or $C_{1-6}$ alkyl.

5. A method according to claim 1 in which R has the formula (IIc)

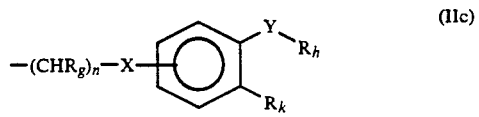

(IIc)

in which
the group $-(CHRg)_n-X-$ is in the meta- or paraposition with respect to $YR_h$ or $R_k$; $R_g$ is hydrogen or $C_{1-6}$ alkyl, n and X are as defined in formula (IIb), Y is $>C=O$, $>CHOH$, $-S=O$ or $SO_2$;
each of $R_h$ and $R_k$ is $C_{1-6}$ alkyl, or
$R_h$ and $R_k$ are linked together and Rh represents $-(Z)m-$ where m is 0 or 1 and Z is O, S or $NR_s$ where $R_s$ is hydrogen or $C_{1-6}$ alkyl, and $R_k$ represents $-(CH_2)_r-$ where r is an integer of from 1 to 4, and in which one or more of the $-(CH_2)-$ groups is optionally substituted by a $C_{1-6}$ alkyl group.

6. A method according to claim 1 in which the compound of formula (Ia) is of formulae (Ic) or (Id):

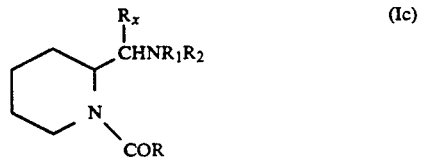

(Ic)

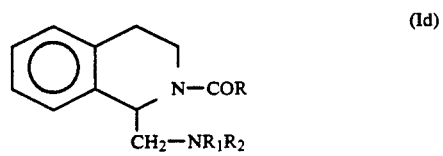

(Id)

in which R, $R_1$, $R_2$ and $R_x$ are as defined with reference to formula (Ia).

7. A method according to claim 1, in which the compound of formula (Ia) is selected from the group consisting of:

(2S)-1-(3,4,-dichlorophenylacetyl)-2-(1-pyrrolidinylmethyl)piperidine;
(2R,S)-1-(4-nitrophenylacetyl)-2-(1-pyrrolidinylmethyl)piperidine;
(2S)-1-(4-trifluoromethylphenylacetyl)-2-(1-pyrrolidinylmethyl)piperidine;
1-(1-pyrrolidinylmethyl)-2-(3,4-dichlorophenylacetyl)-1,2,3,4-tetrahydroisoquinoline;
(−)-1-(1-pyrrolidinylmethyl)-2-(3,4-dichlorophenyl acetyl)-1,2,3,4-tetrahydroisoquinoline;
(−)-1-(1-pyrrolidinylmethyl)-2-(4-trifluoromethylacetyl)-1,2,3,4-tetrahydroisoquinoline;
1-[1-oxo-3,4,-dihydro-(2H)-naphth-6-yl]acetyl-2(pyrrolidin-1-yl)methyl-piperidine; and
1(pyrrolidin-1-yl)methyl-2-(3,4-dichlorophenyl)acetyl-5-hydroxy-1,2,3,4-tetrahydroisoquinoline.

8. A method according to claim 1 in which the compound of formula (Ia) or pharmaceutically acceptable salt or solvate thereof, is administered in unit dose form, each dose containing from 20 to 100 mg of compound.

* * * * *